United States Patent [19]

Aoki et al.

[11] Patent Number: 5,100,441
[45] Date of Patent: Mar. 31, 1992

[54] GAS LIQUID SEPARATOR WITH IMPROVED HOUSING CONFIGURATION

[75] Inventors: Junji Aoki, Kyoto; Hideki Koike, Chikuzendai; Soji Sakamoto, Kyoto, all of Japan

[73] Assignee: Horiba, Ltd., Kyoto, Japan

[21] Appl. No.: 671,477

[22] Filed: Mar. 19, 1991

[30] Foreign Application Priority Data

Mar. 19, 1990 [JP] Japan .................................. 2-28553

[51] Int. Cl.$^5$ ...................... B01D 53/22; B01D 45/14
[52] U.S. Cl. .......................................... 55/158; 55/337; 55/401; 55/406; 55/438; 55/465
[58] Field of Search .................................. 55/400–406, 55/436–438, 465, 158, 159, 184, 185, 192, 337

[56] References Cited

U.S. PATENT DOCUMENTS

| | | | |
|---|---|---|---|
| 2,127,746 | 8/1938 | Logan | 55/403 |
| 3,148,146 | 9/1964 | Asnes et al. | 55/400 X |
| 3,439,477 | 4/1969 | Pyne et al. | 55/406 X |
| 3,518,815 | 7/1970 | McFarland et al. | 55/465 X |
| 3,686,831 | 8/1972 | Libby | 55/403 X |
| 4,102,658 | 7/1978 | Järvenpää | 55/406 X |
| 4,382,804 | 5/1983 | Mellor | 55/400 X |
| 4,402,715 | 9/1983 | Ruyak et al. | 55/400 X |
| 4,530,462 | 7/1985 | Andersson | 55/405 X |
| 4,678,488 | 7/1987 | Howard et al. | 55/406 |
| 4,842,478 | 6/1989 | Durr et al. | 55/406 X |

FOREIGN PATENT DOCUMENTS

| | | | |
|---|---|---|---|
| 56-006327 | 2/1981 | Japan | 55/406 |
| 1505565 | 9/1989 | U.S.S.R. | 55/410 |
| 1549564 | 3/1990 | U.S.S.R. | 55/409 |

Primary Examiner—Robert Spitzer
Attorney, Agent, or Firm—Price, Gess & Ubell

[57] ABSTRACT

An improved gas liquid separator assembly is provided having a housing block with an interior gas liquid separating chamber. A sample gas introducing conduit and a sample gas discharging conduit can extend from the exterior of the housing block to one upper surface of the separating chamber. An opening can extend through the lower end of the housing block from the other side of the separating chamber to the exterior of the housing block. This opening is of a configuration complementary to a detachable mounted motor block for supporting a centrifugal separator. The centrifugal separator can be easily detached for maintenance of the gas liquid separating chamber.

10 Claims, 3 Drawing Sheets

GAS LIQUID SEPARATOR WITH IMPROVED HOUSING CONFIGURATION

BACKGROUND OF THE INVENTION

1. Field of the Invention

The present invention relates to a gas liquid separator, in which a sample gas can be introduced into a gas liquid separating chamber to effectuate a separation of liquids and impurities that may be contained in the sample gas and, more particularly, to a centrifugal separator having an improved body construction that facilitates manufacturing and maintenance of the separator.

2. Description of Related Art

Gas liquid separators have been frequently utilized in the prior art, for example, as a preliminary or auxiliary processing device in determining constituents of combustion exhaust gas from a motor vehicle, to enable the analysis of air pollutants. An exhaust from a motor vehicle can be utilized to determine the performance of the engine and the fuel by measuring concentrations of $CO_2$, $NO_x$, HC and the like contained in the exhaust gas. This measurement is frequently done with an infrared analyzer that is supplied a portion of the exhaust gas as a sample gas. Prior to such an analysis in an infrared analyzer, it is necessary to prepare the sample gas to remove any liquid constituents or liquefactions which can produce an error in the analytical result. In this regard, a highly efficient gas liquid separator is desired.

An example of a conventional gas liquid separator can be seen in FIG. 3. A block body or housing 41 has an upper removable segmented member 42 that is sealed to a cavity in the top of the body 41. This separable block member 42 is mounted above a gas liquid separating chamber 43 formed as a nearly rectangular hollow chamber positioned above a revolving separator disk 54. On one lower side of the gas liquid separating chamber 43 is an exhaust or bypass outlet 44. The separable block member 42 has a pair of conduits 46 and 47 terminating at one end on, respectively, port openings 56 and 57 and, at the other end, on connection portions 48 and 49. Port opening 56 is offset from the axis of the revolving disk 54, and is utilized to introduce a portion of the exhaust gas into the gas liquid separating chamber 43. The port opening 57 is coaxial with the axis of rotation of the revolving disk 54 and can withdraw a portion of the sample gas for subsequent analysis, such as in an infrared analyzer (not shown). Any liquid or solid particulates will be discharged from the surface of the revolving disk 54 to be subsequently collected in a drain pot (not shown) which can be connected with the bypass outlet 44. The interior surface of the separable block member 42 is planar and is offset by a relatively small gap (g) from the surface of the revolving disk 54. The separable block member 42 has a series of sealing members 50 provided on its outer circumference. An upper shoulder or flange portion 50 is of a configuration complementary to the support shoulder 59 on the upper surface of the body block 41.

The centrifugal separator 51 principally comprises the upper revolving disk 54 and a lower motor 52 that is supported within a motor block 53. The motor block 53, in turn, is mounted into a cavity of a complementary configuration within the interior of the body block 41. The relative size of the motor block 53 and the alignment positions of the supporting shoulders 59 and 60 will define the desired small gap (g). As can be appreciated, the revolving disk 54 is rotationally driven at a relatively high speed by the motor 52 so that when sample gas is introduced into the gas liquid separator chamber 43 through the sample gas introducing conduit 46, the sample gas will be subject to a gas liquid separation as a result of contact with the revolving disk 54. This will permit a portion of the sample gas with the liquefaction removed to be withdrawn by the sample gas discharging conduit 47. The connecting portion 49 of the sample gas discharge conduit 47 is connected to an infrared analyzer (not shown).

As mentioned above, the liquefaction and any solid particulate material can be removed from the drain pot (not shown).

As can be readily appreciated, such a manner of separating sample gas from liquids and particulate material in the exhaust of the engine of a motor vehicle could result in an accumulation of impurities and foreign matter. Thus, the revolving disk 54 of the centrifugal separator is prone to be soiled and damaged so that the dimensions of the gap (g) formed between the upper surface 55 of the revolving disk 54 and the lower end face 58 of the separable block member 42 can become clogged or diminished in size so that the gas liquid separating characteristics are deteriorated. It is frequently necessary to service and maintain the gas liquid separating chamber 43 and the component parts by cleaning and removing any accumulated debris.

During this maintenance cycle, the separable block member 42 must be separated from the body block 41 such as shown by the dotted lines in FIG. 3. When this occurs, it is necessary to remove any connecting pipes between the exhaust engine and the infrared analyzer that are connected, respectively, to coupling portions 48 and 49. The necessity of breaking down the constituent parts of the liquid gas separator and connecting and disconnecting the various pipes can be relatively troublesome and time consuming to the operator.

An additional maintenance problem occurs when it becomes necessary to repair or to replace the motor 52. The revolving disk 54 of the centrifugal separator 51 can typically operate at a relatively high speed of, for example, 11,000 to 13,000 rpm. Under such conditions, the motor can deteriorate. The motor, however, is positioned in the interior of the body block 41. To gain access to it, the separable member 42 and the motor block 53 must be removed. Thus, the prior art is still seeking a solution to the above problems.

SUMMARY OF THE INVENTION

It is an object of the present invention to provide a gas liquid separator that is capable of easily carrying out a maintenance procedure without requiring the removal and reconnection of the various pipes with the body block during normal maintenance procedures such as cleaning the gas liquid separating chamber.

It is a further object of the present invention to simplify the construction of the body block to obviate the necessity to connect and disconnect sample gas introducing and discharging conduits while facilitating both the maintenance of the gas liquid separating chamber and operational maintenance of the centrifugal motor.

It is a further object of the present invention to provide a body block member wherein the sample gas introducing conduit and the sample gas discharging conduit can be formed in the body block, and the centrifugal separator can be detachably mounted on the body block through the motor block.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

DESCRIPTION OF THE PREFERRED EMBODIMENTS

The following description is provided to enable any person skilled in the industrial measurement field to make and use the invention and sets forth the best modes contemplated by the inventors of carrying out their invention. Various modifications, however, will remain readily apparent to those skilled in this field, since the generic principles of the present invention have been defined herein specifically to provide a relatively easily manufactured and maintained gas liquid separator.

Figure 1:
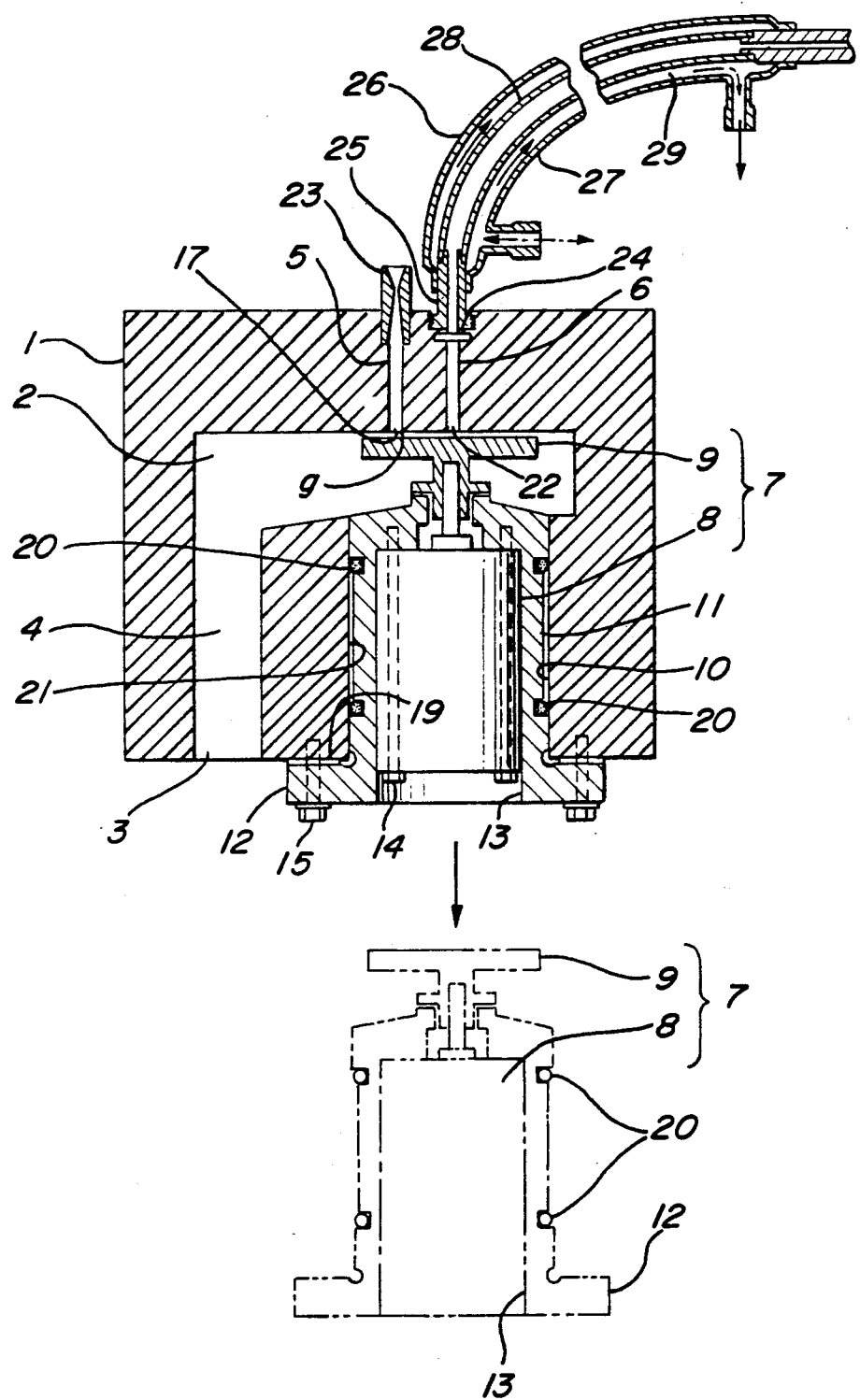
FIG. 1 is a cross-sectional view showing a gas liquid separator according to one preferred embodiment of the present invention.

Referring to FIG. 1, a gas liquid separator assembly is disclosed having a housing block or body block 1 made of, for example, aluminum. The body block 1 has an interior cavity which performs the function of a gas liquid separating chamber 2 and is of a nearly rectangular configuration. The separating chamber 2 is connected by a bypass conduit 4 that terminates in a bypass outlet or port 3 at the bottom of the body block 1. Adjacent an upper surface of the separating chamber 2 is a conduit or passageway 5 for introducing a sample gas into the chamber 2. Also, a sample gas discharge conduit or passageway 6 extends from the gas liquid separating chamber 2 to the exterior upper surface of the body block 1.

Mounted within the body block 1 is a centrifugal separator 7 that comprises a motor 8 and an upper revolving disk 9 that is positioned immediately adjacent the upper surface of the gas separating chamber 2, the interior port openings of the sample gas introducing conduit 5, and the sample gas discharging conduit 6. A relatively small space or gap (g) is provided between the upper surface of the disk 9 and the upper surface of the gas liquid separating chamber 2. To accommodate the centrifugal separator 7, the body block 1 has a complementary aperture or fitting hole 10 that extends from the lower surface of the body block 1 into the gas liquid separating chamber 2. A motor block 11 is closely fitted within the fitting hole 10, and annular grooves can support appropriate seals 20 for extending between the outer surface of the motor block 11 and a wall surface 21 of the fitting hole 10.

The motor block 11 can also be made of, for example, aluminum or other appropriate metal, and is provided with a flange member 12 on its lower end side thereof. The motor block 11 also has a hollow opening 13 which is accessible from the bottom side of the body block 1. The motor 8 can be mounted in the motor block 11 by means of a screw or bolt 14 or, alternatively, can be fixedly adhered therein by the use of an epoxy resin. The motor block 11 with the motor 8 securely fastened to the motor block 11 can be further secured into the fitting hole 10 of the body block 1 by means of bolts or screws 15 that can extend through apertures in the flange 12. The flange 12 can directly bear upon the supporting surface 19 on the lower portion of the body block 1. The relative dimensions and positioning of the flange 12 and the support surface 19 will define the dimensions of the gap (g) between the revolving disk 9 and the opening port 17 on the inner side of the sample gas introducing conduit 5 and the opening port 22 on the inner side of the sample gas discharging conduit 6.

As can be appreciated, the axis of the sample gas introduction conduit 5 is offset from the axis of rotation of the motor 8. In this regard, the portion of sample gas introduced into the gas liquid separating chamber having, for example, liquids and solid particulates, will cause the liquids and solid particulates to strike the rotating disk 9 and to be radially discharged through the bypass conduit 4 to a receptacle (not shown). The gas portion of the combustion sample can then be withdrawn through the gas discharging conduit 6 for subsequent analysis.

As shown in FIG. 1, a choke member 23, such as a Venturi tube, can be provided on the outside upper surface of the sample gas introducing conduit 5 to control or regulate the input pressure of the sample gas from a sample gas supply source such as a combustion engine (not shown). In addition, a filter unit 24 can also be fastened on the outer side of the sample gas discharging conduit 6 to further remove any foreign solid particulates which are not separated as a result of the action of the centrifugal separator 7. A semipermeable dehumidifier 26 can be connected through a connecting portion 25 to the filter 24. The semipermeable dehumidifier 26 is a double tube or concentric bitube structure and includes an inner tube 28 formed of a semipermeable membrane and an outer tube, so that any moisture that is found concentrated within the sample gas being discharged through the inner tube 28 may be further reduced by the flow of dry air or nitrogen gas through the passage 29 between said outer tube 27 and the inner tube 28.

Although not shown in FIG. 1, it is to be understood that a connecting pipe to the choke member 23 can lead to the source of the sample gas, while a further pipe can be connected to the semipermeable dehumidifier 26 to lead the prepared gas specimens to an analyzer such as an infrared analyzer.

In operation, a specimen of a sample gas, such as a combustion exhaust, is supplied to the sample gas introducing conduit 5 through the pressure reducing choke 23. Contaminants in the sample gas, such as liquid and solid particles, can be subject to centrifugal separation as a result of the revolving disk 9. The revolving disk 9 will rotate at a relatively high speed, and the gas portion of the sample will have substantially all of its liquefaction and larger solid particulates discharged through the bypass conduit 4 to a drain pot (not shown). The gas portion of the sample will be discharged through the sample gas discharging conduit 6 and will be further treated as a result of the filter 24 and the semipermeable dehumidifier 26 prior to analysis in, for example, an infrared analyzer (not shown).

During the normal use of the gas liquid separator, a buildup of solid particulates can occur in the gas liquid separator chamber 2. This debris can interfere with the performance of the gas liquid separator. A normal maintenance cycle would require the inside of the gas liquid separator chamber 2 to be cleaned, for example, by a washing mode of operation. To facilitate this maintenance cycle without requiring a disconnection to the source of the sample gas and the apparatus providing subsequent treatment of the separated gas portion of the sample, it is possible to remove the bolts 15 and to lower the centrifugal separator 7 as shown in the dotted lines in FIG. 1. As can be appreciated, the choke 23 and the filter 24, along with the semipermeable dehumidifier 26, can be built into the connecting lines to improve the capacity of the gas liquid separator. These elements can be alternatively fixedly integrated within the body block 1 so that the gas liquid separator can be further compacted in its construction.

Figure 2:
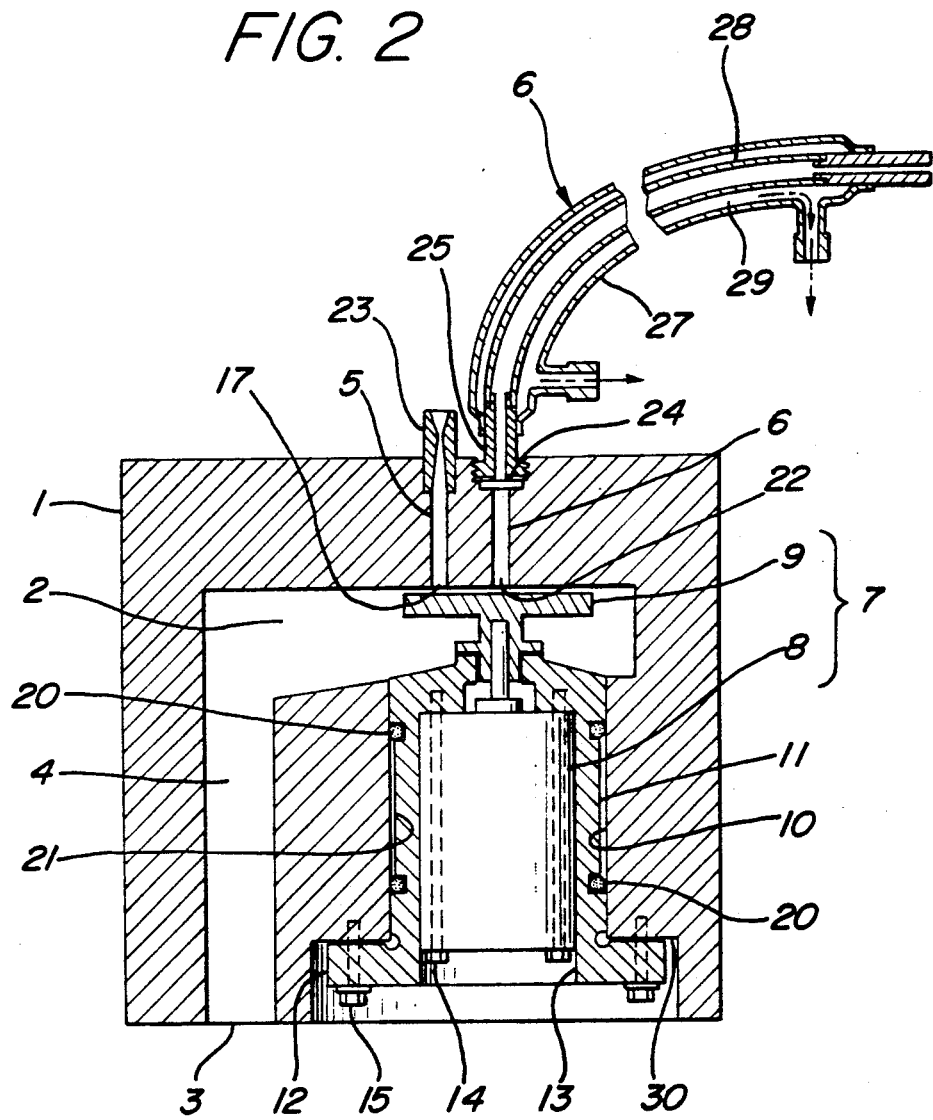
FIG. 2 is a cross-sectional view showing the gas liquid separator according to another embodiment of the present invention.
Figure 3:
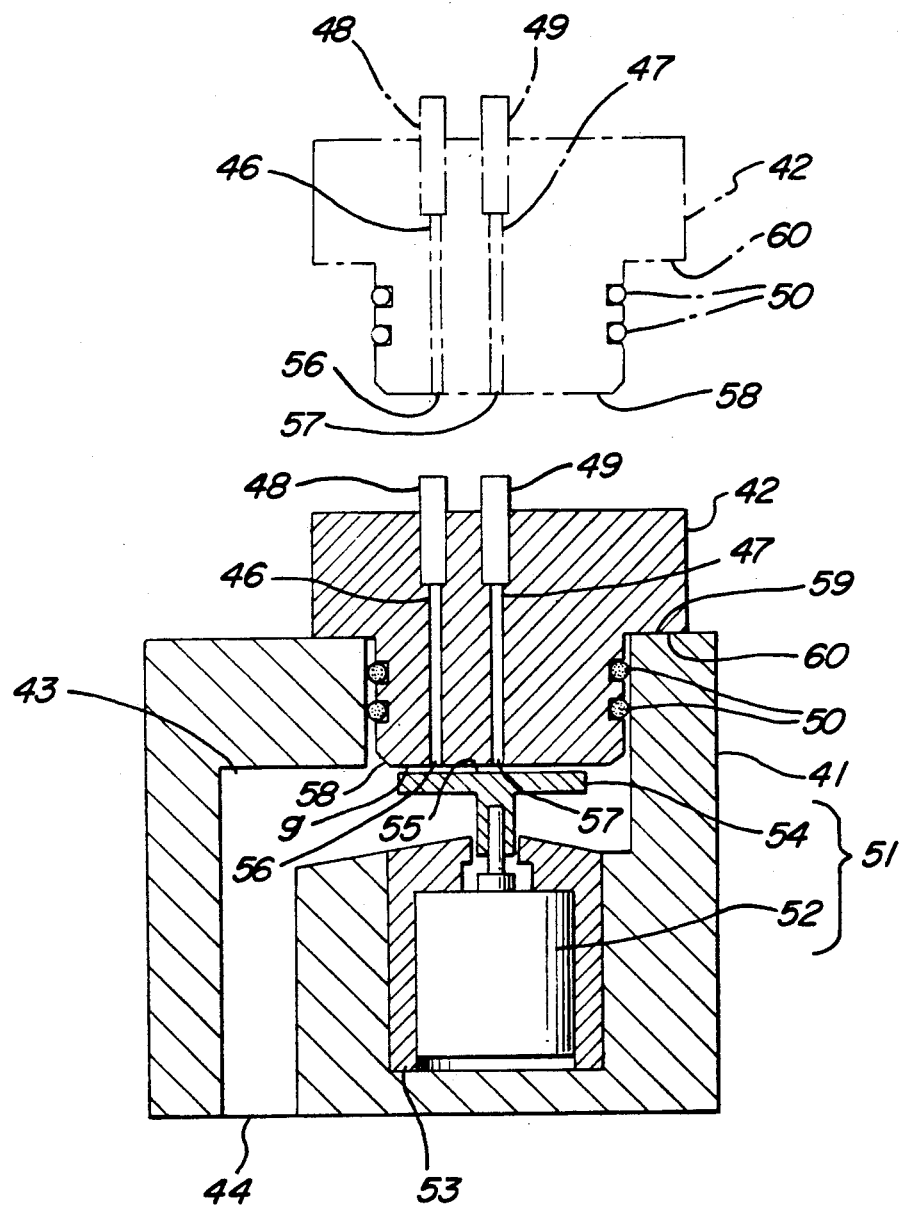
FIG. 3 is a cross-sectional view showing a conventional example of the prior art.

Referring to FIG. 2, an alternative embodiment of the present invention is disclosed, and like reference numbers refer to like reference parts. In this embodiment, the fitting hole 10 is further provided with a stepped portion 30 to thereby enable the motor block 11 to be completely housed within the body block 1. Thus, the lower surface of the motor block 11 is recessed from the supporting bottom surface of the body block 1.

As a result of the present invention, the body block 1 can be provided with a sample gas introducing conduit and a sample gas discharging conduit of a relatively permanent configuration, and the centrifugal separator 7 can be conveniently detachably mounted from the bottom of the body block 1 through release of the motor block 11. The inside of the gas liquid separating chamber 2 can be easily washed and inspected. Thus, maintenance can be facilitated when compared with the prior designs used in gas liquid separators.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. A gas liquid separator comprising:
    a housing block having an interior gas liquid separator chamber, a sample gas introducing conduit, and a sample gas discharging conduit, the respective conduits extending through the housing block and opening into the separating chamber;
    the housing block further having an opening extending from the gas liquid separating chamber on the opposite side of the introducing and discharging conduits to the exterior of the housing block;
    a detachably mounted motor block of a configuration complementary in shape to the opening is mounted in the opening;
    a centrifugal separator, and
    a motor mounted in the motor block to drive the centrifugal separator, whereby the interior gas liquid separating chamber can be readily accessed for maintenance.

2. The invention of claim 1, further including alignment means on a lower surface of the housing block and a flange on the motor block to enable a precise positioning of the motor block in the housing block.

3. The invention of claim 2, further including a stepped opening on the housing block of a dimension to receive the flange of the motor block.

4. The invention of claim 1, further including a Venturi tube connected to the sample gas introducing conduit and a filter and a semipermeable dehumidifier connected to the sample gas discharge conduit.

5. The invention of claim 1, wherein said motor is detachably mounted in said motor block.

6. An improved gas liquid separator assembly comprising:
    a housing block having an interior gas liquid separating chamber, a sample gas introducing conduit, and a sample gas discharging conduit, the respective conduits extending through the housing block and opening into the separation chamber, the housing block further having an opening extending from the gas liquid separating chamber on the opposite side of the introducing and discharging conduits to the exterior of the housing block;
    a dehumidifier mounted on the surface of the housing block and connected to the sample gas discharging conduit,
    a detachably mounted motor block of a configuration complementary in shape to the opening mounted in the opening;
    a centrifugal separator assembly, and
    a motor mounted in the motor block, to drive the centrifugal separator, whereby the interior gas liquid separating chamber can be readily accessed for maintenance.

7. The invention of claim 6, further including alignment means on a lower surface of the housing block and a flange on the motor block to enable a precise positioning of the motor block in the housing block.

8. The invention of claim 6, further including a Venturi tube connected to the sample gas introducing conduit and a filter connected to the sample gas discharge conduit.

9. The invention of claim 8, further including a stepped opening on the housing block of a dimension to receive the flange of the motor block.

10. The invention of claim 9, wherein said motor is detachably mounted in said motor block.

* * * * *